(12) United States Patent
Hurwitz

(10) Patent No.: US 9,220,713 B2
(45) Date of Patent: Dec. 29, 2015

(54) COMPOSITIONS AND METHODS FOR THE TREATMENT OF DRUG-INDUCED HAND-FOOT SYNDROME

(75) Inventor: Herbert Hurwitz, Hillsborough, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 13/502,209

(22) PCT Filed: Oct. 15, 2010

(86) PCT No.: PCT/US2010/052836
§ 371 (c)(1),
(2), (4) Date: Jun. 27, 2012

(87) PCT Pub. No.: WO2011/047256
PCT Pub. Date: Apr. 21, 2011

(65) Prior Publication Data
US 2012/0258970 A1  Oct. 11, 2012

Related U.S. Application Data

(60) Provisional application No. 61/279,091, filed on Oct. 16, 2009.

(51) Int. Cl.
*A61K 31/519* (2006.01)
*A61K 45/06* (2006.01)

(52) U.S. Cl.
CPC .............. *A61K 31/519* (2013.01); *A61K 45/06* (2013.01)

(58) Field of Classification Search
None
See application file for complete search history.

(56) References Cited

U.S. PATENT DOCUMENTS

| | | |
|---|---|---|
| 8,623,878 B2 | 1/2014 | Rodemar |
| 2002/0028237 A1 | 3/2002 | Colbern et al. |
| 2007/0225217 A1 | 9/2007 | Chappell et al. |
| 2008/0188480 A1 | 8/2008 | Black |
| 2009/0048179 A1 | 2/2009 | Black |
| 2009/0197922 A1 | 8/2009 | Maitland et al. |

FOREIGN PATENT DOCUMENTS

| | | | |
|---|---|---|---|
| WO | WO 02/060422 | * | 8/2002 |
| WO | WO 2007/138103 A1 | | 12/2007 |

OTHER PUBLICATIONS

Webster-Gandy (European Journal of Oncology Nursing (2007), 11, 238-246).*
Boswell-Smith et al. Phosphodiesterase inhibitors. British Journal of Pharmacology, 2006, 147, S252-S257.*
Ghofrani et al. Differences in hemodynamic and oxygenation responses to three different phosphodiesterase-5 inhibitors in patietns with pulmonary arterial hypertension: a randomized prospective study. Journal of American College of Cardiology, vol. 44, No. 7, 2004.*
European Search Report Corresponding to European Patent Application No. 10 82 4160; Dated: Feb. 1, 2013; 10 Pages.
Gomberg-Maitland et al. "A dosing/cross-development study of the multikinase inhibitor sorafenib in patients with pulmonary arterial hypertension" *Clinical Pharmacology & Therapeutics* 87(3):303-310 (2010).
Lee et al. "Sildenafil attenuates renal injury in an experimental model of rat cisplatin-induced nephrotoxicity" *Toxicology* 257(3):137-143 (2009).
Lipworth et al. "Hand-Foot Syndrome (Hand-Foot Skin Reaction, Palmar-Plantar Erythrodysesthesia): Focus on Sorafenib and Sunitinib" *Oncology* 77(5):257-271 (2009).
Moffat et al. "Inhibition in vitro of cyclic 3', 5' nucleotide phosphodiesterase activity by drugs" *Eur. J. Toxicol.* 5(3):160-62 (1972).
Pusztai et al. "Phase I and II study of exisulind in combination with capecitabine in patients with metastatic breast cancer" *Journal of Clinical Oncology*, 21(18):3454-3461 (2003).
Farr et al. "Palmar-Plantar Erythrodysesthesia Associated with Chemotherapy and its Treatment" *Case Rep Oncol* 4:229-235 (2011).
Lacouture et al. "Evolving Strategies for the Management of Hand-Foot Skin Reaction Associated with the Multitargeted Kinase Inhibitors Sorafenib and Sunitinib" *The Oncologist* 13:1001-1011 (2008).
Lorusso et al. Pegylated Liposomal Doxorubicin-Related Palmar-Plantar Erythrodysesthesia ('Hand-Foot' Syndrome) Anals of *Oncology* 18:1159-1164 (2007).
Walko et al. "Capecitabine: a Review" *Clin Ther*. 27(1):23-44 (2005) (Abstract).
International Search Report and Written Opinion dated Dec. 6, 2010 for International Application No. PCT/US2010/052836 (10 pages).
International Preliminary Report on Patentability dated Apr. 26, 2012 for International Application No. PCT/US2010/052836 (7 pages).
Adrucil (fluorouracil) package insert, Aug. 2012 (6 pages).
Anderson et al. "Search for Evidence-Based Approaches for the Prevention and Palliation of Hand-Foot Skin Reaction (HFSR) Caused by the Multikinase Inhibitors (MKIs)" *The Oncologist* 14(3):291-302 (2009).
Escudier et al. "Sorafenib in Advanced Clear-Cell Renal-Cell Carcinoma" *The New England Journal of Medicine* 356:25-134 (2007).
Galie et al. "Sildenafil Citrate Therapy for Pulmonary Arterial Hypertension" *The New England Journal of Medicine* 358:2148-2157 (2005).
Galie et al. "Tadalafil Therapy for Pulmonary Arterial Hypertension" *Circulation* 119:2894-2903 (2009).

(Continued)

*Primary Examiner* — Anna Pagonakis
(74) *Attorney, Agent, or Firm* — Myers Bigel Sibley & Sajovec, P.A.

(57) ABSTRACT

The present invention provides methods of treating, ameliorating or preventing hand-foot syndrome in a subject in need thereof comprising administering to the subject a therapeutically effective amount of a phosphodiesterase inhibitor.

1 Claim, No Drawings

(56) References Cited

OTHER PUBLICATIONS

Jing et al. "Vardenafil treatment for patients with pulmonary arterial hypertension: a multicentre, open-label study" *Heart* 95:1531-1536 (2009).

Lacouture et al. "Hand foot skin reaction in cancer patients treated with the multikinase inhibitors sorafenib and sunitinib" *Annals of Oncology* 19(11):1955-1961 (2008).

Masson et al. "PDE-5 Inhibitors: Current Status and Future Trends" *Urologic Clinics of North America* 32:511-525 (2005).

Erectile Dysfunction Guideline Update Panel "The Management of Erectile Dysfunction: An Update" *America Urological Association Education and Research, Inc.* Chapter 1 (2007) (35 pages).

Motzer et al. "Sunitinib versus Interferon Alfa in Metastatic Renal-Cell Carcinoma" *The New England Journal of Medicine* 356(2):115-124 (2007).

Paick et al. "Efficacy and Safety of Mirodenafil, A New Oral Phosphodiesterase Type 5 Inhibitor, for Treatment of Erectile Dysfunction" *The Journal of Sexual Medicine* 5:2672-2680 (2008).

Prescribing Information: Adcirca (tadalafil) Dec. 2013 (14 pages).
Prescribing Information: Cometriq (cabozantinib) Nov. 2012 (24 pages).
Prescribing Information: Doxil (doxorubic HCl liposome injection) Aug. 2013 (15 pages).
Prescribing Information: Inlyta (axitinib) Sep. 2013 (19 pages).
Prescribing Information: Levitra (vardenafil hydrochloride) Aug. 2013 (10 pages).
Prescribing Information: Nexavar (sorafenib) Oct. 2010 (19 pages).
Prescribing Information: Revatio (sildenafil) Jan. 2014 (30 pages).
Prescribing Information: Stendra (avanafil) Jun. 2013 (22 pages).
Prescribing Information: Stivarga (regorafenib) Aug. 2013 (22 pages).
Prescribing Information: Sutent (sunitinib malate) Aug. 2013 (29 pages).
Prescribing Information: Tafinlar (dabrafenib) Jan. 2014 (43 pages).
Prescribing Information: Votrient (pazopanib) Apr. 2012 (32 pages).

Saltz et al. "Bevacizumab in Combination With Oxaliplatin-Based Chemotherapy as First-Line Therapy in Metastatic Colorectal Cancer: A Randomized Phase III Study" *Journal of Clinical Oncology* 26(12):2013-2019 (2008).

Wright, P. J. "Comparison of phosphodiesterase type 5 (PDE5) inhibitors" *International Journal of Clinical Practice* 60(8):967-975 (2006).

* cited by examiner

COMPOSITIONS AND METHODS FOR THE TREATMENT OF DRUG-INDUCED HAND-FOOT SYNDROME

PRIORITY STATEMENT

The present invention is a 35 U.S.S. §371 national phase application of International Application Serial No. PCT/US2010/052836, filed Oct. 15, 2010, which claims the benefit, under 35 U.S.C. §119(e), of U.S. Provisional Application Ser. No. 61/279,091, filed Oct. 16, 2009, the entire contents of each of which are incorporated by reference herein.

FIELD OF THE INVENTION

The present invention is directed to compositions and methods for the treatment of drug-induced hand/foot syndrome using phosphodiesterase inhibitors.

BACKGROUND OF THE INVENTION

Palmar-plantar erythrodysesthesia (PPE), also known as hand-foot syndrome (HFS), is a frequent dermatologic toxicity wherein the tissues of the palms and soles become red, painful and thickened, with possible blistering and peeling of the skin.

PPE is associated with many commonly used anticancer agents, particularly the VEGF-kinase inhibitors sorafenib (Nexevar™) and sunitinib (Sutent™), infusional 5-fluoracil (5-FU), capecitabine (Xeloda™), and liposomal doxorubicin (Doxil™). Over 400,000 patients worldwide are treated with these agents each year. PPE is among the most common reasons for dose holding, dose reduction and/or treatment discontinuation for these anti-cancer agents. The frequency of any grade (grade 1-3) PPE is up to 21% for sunitinib, 30% for sorafenib, 54% for capecitabine, and 51% for liposomal doxorubicin (1-4). The frequency of severe (grade 3) PPE is seen in up to 5% of patients for sunitinib, 8% for sorafenib, 17% for capecitabine and 24% for liposomal doxorubicin (1-7). Thus, PPE represents an important toxicity not only because of the suffering it causes directly, but also because this toxicity often limits the potential benefits of otherwise effective anti-cancer therapies.

The standard of care for the management of PPE currently includes only the use of emollients and discontinuation or dose reduction of the relevant anti-cancer treatment. More effective, mechanism based treatments for PPE are urgently needed.

The present invention overcomes previous shortcomings in the art by providing compositions and methods of treating PPE and/or drug toxicity associated reactions, disorders and/or symptoms in a subject.

SUMMARY OF THE INVENTION

The present invention provides compositions and methods for the treatment, amelioration, and/or prevention of conditions characterized by PPE (e.g., drug-induced PPE) in a subject.

One aspect of the present invention provides a method of treating PPE in a subject (e.g., a subject in need thereof), comprising, consisting of, or consisting essentially of administering to the subject an effective amount of a phosphodiesterase inhibitor, thereby treating PPE in the subject.

Another aspect of the present invention provides a method of ameliorating PPE in a subject (e.g., a subject in need thereof), comprising, consisting or, or consisting essentially of administering to the subject an effective amount of a phosphodiesterase inhibitor, thereby ameliorating PPE in the subject.

Another aspect of the present invention provides a method of preventing PPE in a subject (e.g., a subject in need thereof), comprising, consisting of, or consisting essentially of administering to the subject an effective amount of a phosphodiesterase inhibitor, thereby preventing PPE in the subject.

In certain embodiments of this invention, the PPE is drug-induced.

An additional aspect of the present invention provides a method of treating a drug toxicity associated reaction, disorder and/or symptom in a subject (e.g., a subject in need thereof), comprising, consisting of, or consisting essentially of administering to the subject an effective amount of a phosphodiesterase inhibitor, thereby treating the drug toxicity associated reaction, disorder and/or symptom in the subject.

A further aspect of the present invention provides a method of ameliorating a drug toxicity associated reaction, disorder and/or symptom in a subject (e.g., a subject in need thereof), comprising, consisting or, or consisting essentially of administering to the subject an effective amount of a phosphodiesterase inhibitor, thereby ameliorating the drug toxicity associated reaction, disorder and/or symptom in the subject.

Yet another aspect of the present invention provides a method of preventing a drug toxicity associated reaction, disorder and/or symptom in a subject (e.g., a subject in need thereof), comprising, consisting of, or consisting essentially of administering to the subject an effective amount of a phosphodiesterase inhibitor, thereby preventing the drug toxicity associated reaction, disorder and/or symptom in the subject.

Additionally provided herein is the use of a phosphodiesterase inhibitor in the treatment, amelioration and/or prevention of PPE and/or a drug toxicity associated reaction, disorder and/or symptom in a subject (e.g., a subject in need thereof).

Further provided herein is the use of a phosphodiesterase inhibitor in the manufacture of a medicament for the treatment, amelioration and/or prevention of PPE and/or a drug toxicity associated reaction, disorder and/or symptom in a subject (e.g., a subject in need thereof).

DETAILED DESCRIPTION OF THE INVENTION

For the purposes of promoting an understanding of the principles of the present invention, reference will now be made to exemplary embodiments and specific language will be used to describe the same. It will nevertheless be understood that no limitation of the scope of the disclosure is thereby intended, such alteration and further modifications of the invention as illustrated herein, being contemplated as would normally occur to one skilled in the art to which the disclosure relates.

Articles "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. The term "nonhuman animals" includes all vertebrates, e.g., mammals and non-mammals, such as non-human primates, sheep, dog, pig, cat, horse, cow, chickens, amphibians, reptiles, rodents (e.g., mice, rats, etc.) and the like. In particular embodiments, the subject of this invention is a human subject.

A drug of this invention can be, but is not limited to a chemotherapeutic drug, an anti-cancer drug, an anti-neoplastic drug, an anti-angiogenesis drug, an anti-vascular drug, an anti-infective drug, a liposomal drug, a liposomal antifungal drug, an anti-vascular epithelial growth factor (anti-VEGF) drug, a drug associated with PPE, and/or any other drug now known or later identified that is known or believed to be associated with PPE and/or with a reaction, condition, disorder and/or symptom of drug toxicity, and any combinations thereof A drug "associated with PPE" can be any drug that is known or believed to produce and/or exacerbate the symptoms of PPE, alone and/or in combination with other drugs, as described herein. A drug associated with drug toxicity can be any drug that is known or believed to produce and/or exacerbate a reaction, disorder and/or symptom associated with drug toxicity, alone or in combination with other drugs, as described herein.

In some embodiments, a drug of this invention can be a drug that may not be associated with PPE and/or the other reactions disorders and/or symptoms described herein when given at lower doses and/or when given by other than intravenous infusion and/or when given in the absence of other drugs that are associated with PPE and/or the reactions, disorders and/or symptoms described herein, but becomes associated with PPE and/or the other reactions disorders and/or symptoms described herein when given at higher doses and/or when given by intravenous infusion (e.g., continuous intravenous infusion) and/or when given with other drugs that are associated with PPE and/or the reactions, disorders and/or symptoms described herein.

The clinical symptoms of PPE and methods of diagnosing PPE are known in the art. Symptoms of PPE include but are not limited to the appearance, onset, development and/or worsening (e.g., exacerbation) of redness, tenderness, dryness, burning, sores, ulcers, swelling, peeling, cracking, blistering, numbness, tingling, thickening, hardening and pain.

The clinical symptoms of drug toxicity and methods of diagnosing drug toxicity associated reactions and/or disorders are known in the art. Drug toxicity associated reactions, disorders and/or symptoms of this invention include but are not limited to the appearance, onset, development and/or worsening (e.g., exacerbation) of fatigue, migraine, gastrointestinal toxicities (e.g., diarrhea, enteritis, colitis, fistulae/gastrointestinal perforation, etc.), perforation or fistulae formation of the intestine and/or other organs (e.g., nasal septum, trachea, lung, etc.), abnormal or delayed wound healing, bleeding (e.g., ranging from minor to severe mucosal bleeding (e.g., nose bleed, hemorrhoids), hemoptosis, upper gastrointestinal bleeding, tumor bleeding, etc., renal toxicities (e.g., proteinuria, nephritic syndrome, renal insufficiency due to alterations in renal hemodynamics or glomerular or renal tubule blood flow and/or permeability, glomerular damage, etc.), anti-vascular endothelial growth factor (anti-VEGF) toxicities, anti-angiogenesis toxicities, cardiovascular complications, arterial thromboembolic events (e.g., myocardial infarction, angina, cardiac ischemia, cerebrovascular event, transient ischemic event, stroke, cerebral ischemia, etc.), cerebrovascular complications and the like, including any combination thereof, as would be known in the art.

The reactions, disorders and symptoms described herein can be the result of radiation therapy, alone or in conjunction with chemotherapy or other drug therapy, as is known in the art. Thus, the phosphodiesterase inhibitors of this invention can be employed in the methods described herein to treat, ameliorate and/or prevent such radiation associated reactions, disorders and/or symptoms.

Nonlimiting examples of a drug of this invention associated with PPE and/or with drug toxicity associated reactions, disorders and/or symptoms include sorafenib, sunitinib, pazopanib, linifanib, bevacizumab, 5-fluorouracil, capecitabine, floxuridine, araC, liposomal araC, doxorubin, daunorubicin, idarubicin, liposomal doxorubicin, irniotecan, topotecan, liposomal amphotericin B (e.g., AmBisome; Fungisome, Amphotec, Abelcet, Ampholip), interleukin-2 (IL-2), idarubicin and any combination thereof. Further nonlimiting examples of a drug of this invention include abraxane, anti-estrogens, anthracyclins, azacitidine, azathioprine, bleomycin, busulfan, carbexataxel, carboplatin, cisplatin, chlorambucil, cyclophosphamide, cytarabine, dacarbazine, docetaxel, doxifluridine, epirubicin, epothilone, etoposide, gemcitabine, hydroxyurea, imatinib, interferons, mechlorethamine, melphalan, mercaptopurine, methotrexate, mitomycin C, mitoxantrone, oxaliplatin, paclitaxel, pemetrexed, retinoic acid, taxotere, tamoxifen, teniposide, thiotepa, tioguanine, valrubicin, vinblastine, vincristine, vindesine, and vinorelbine, as well as any other drug now known or later identified to be associated with PPE and/or drug toxicity associated reactions, disorders and/or symptoms, including any combination thereof. Nonlimiting examples of combinations of this invention include 1) bevacizumab and 5-fluorouracil, 2) bevacizamub and capecitabine, and 3) oxaliplatin and 5-fluorouracil.

Nonlimiting examples of a phosphodiesterase inhibitor [e.g., a phosphodiesterase type 5 (PDE-5) inhibitor] of this invention include sildenafil, sildenafil citrate, lodenafil, mirodenafil, avanafil, tadalafil, vardenafil, udenafil and any combination thereof.

In the methods of the present invention, the phosphodiesterase inhibitor can be administered to the subject by any suitable means, such as e.g., topically, orally and/or parenterally. Topical administration can be employed to treat or prevent PPE and/or drug toxicity associated reactions, disorders and/or symptoms. Oral and/or potential (e.g., intravenous) administration can also be employed not only to treat or prevent PPE but also in some embodiments to treat or prevent systemic toxic reactions and/or related symptoms associated with use of the drugs of this invention.

For topical administration of the phosphodiesterase inhibitor, a dose in the range of about 0.0001% to about 20% can be used. For example, in some embodiments, a dose in the range of about 0.005% to about 5% can be used and in some embodiments, a dose in the range of about 0.05% to about 2% can be used. For oral or parenteral administration of the phosphodiesterase inhibitor, a dose in the range of about 1 μg to about 500 mg can be used. For example, in some embodiments, a dose in the range of about 0.5 mg to about 100 mg can be used and in some embodiments, a dose in the range of about 1 mg to about 50 mg can be used. Administration can be one or more times daily, one or more times weekly, one or more times monthly, etc., as indicated according to clinical parameters known in the art.

Various topical formulations are possible. The formulations may include creams and ointments of various concentrations. Topical formulations may be applied using drug embedded into patches and/or other coverings. Nonlimiting examples of a cream of this invention include amantyl cream and cold cream (e.g., an emulsion of oil, wax and water).

In representative embodiments, one application is for dermatologic vascular toxicities associated with a drug of this invention (e.g., chemotherapy and/or anti-angiogenic agents). A direct extension of this approach is the treatment of short and long term radiation induced toxicities, which are thought to be related to radiation induced vascular injury. Treatment of mucositis (including proctitis, vaginitis, cystitis) may also be possible with other local delivery approaches, including locally administered solutions or pastes.

A "subject in need thereof" or "a subject in need of" is a subject known to be, or suspected of having or developing PPE and/or other drug-toxicity associated and/or radiation associated disorders and/or symptoms or at risk of developing PPE and/or other drug toxicity associated or radiation associated disorders and/or symptoms as described herein. In representative embodiments, a subject of this invention can also include a subject not previously known or suspected to have PPE and/or other drug toxicity associated or radiation associated disorders and/or symptoms or in need of treatment for PPE and/or other drug toxicity associated and/or radiation associated disorders and/or symptoms.

A subject of this invention is also a subject known to have PPE and/or other drug toxicity associated disorders and/or symptoms or believed to be at risk of having or developing PPE and/or other drug toxicity associated disorders and/or symptoms. In particular embodiments, a subject in need thereof according to the present invention is a subject who is receiving a drug or drugs that are associated with PPE and/or other drug toxicity associated disorders and/or symptoms, as such drugs are known in the art and as described herein. In certain embodiments of this invention, a subject is a subject diagnosed with or suspected of having cancer, as well as a subject undergoing treatment for cancer. In some embodiments, the subject is a subject diagnosed with or suspected of having a disorder or condition for which treatment with a drug associated with PPE or with other toxicity reactions, disorders or symptoms as described herein is indicated, as well as a subject to whom such a drug of this invention is being or is going to be administered. The subject of this invention can also be a subject diagnosed with or suspected of having a disorder for which radiation treatment is indicated, as well as a subject about to or already undergoing radiation treatment.

In particular embodiments, a subject of this invention can be administered the compositions of this invention even if it is not known or suspected that the subject has PPE and/or other drug-toxicity associated or radiation associated disorders or symptoms (e.g., prophylactically).

Drug toxicity associated reactions, disorders and/or symptoms to be treated, ameliorated and/or prevented with the methods and compositions of this invention are described herein (see, e.g., paragraph 17 above and paragraph 55 in the Examples section provided herein) and are also known in the art. Such reactions, disorders and/or symptoms can be present in a subject of this invention (e.g., a subject in need thereof) along with symptoms of PPE or in the absence of symptoms of PPE. Administration of one or more phosphodiesterase inhibitors of this invention to the subject can be by any suitable route (e.g., orally to treat systemic reactions, disorders and/or symptoms and/or locally (e.g., topically to treat mucosal surfaces such as in the mouth, bladder, vagina, bowel, etc.). For example, one or more phosphodiesterase inhibitors can be administered to a subject both topically and systemically (e.g., orally) to treat, ameliorate and/or prevent PPE and/or other drug toxicity associated reactions, disorders and/or symptoms in the subject.

Thus, the present invention further provides a method of treating, ameliorating and/or preventing a drug toxicity associated and/or radiation associated reaction, disorder and/or symptom in a subject (e.g., a subject in need thereof), comprising administering to the subject an effective amount of a phosphodiesterase inhibitor to the subject, thereby treating, ameliorating and/or preventing the drug toxicity associated and/or radiation associated reaction, disorder and/or symptom in the subject.

In further embodiments, the present invention provides methods of treating, ameliorating and/or preventing disorder, condition and/or symptom as described herein that is not drug-induced (e.g., fatigue, migraine, gastrointestinal toxicities (e.g., diarrhea, enteritis, colitis, fistulae/gastrointestinal perforation, etc.), perforation or fistulae formation of the intestine and/or other organs (e.g., nasal septum, trachea, lung, etc.), abnormal or delayed wound healing, bleeding (e.g., ranging from minor to severe mucosal bleeding (e.g., nose bleed, hemorrhoids), hemoptosis, upper gastrointestinal bleeding, tumor bleeding, etc., renal toxicities (e.g., proteinuria, nephritic syndrome, renal insufficiency due to alterations in renal hemodynamics or glomerular or renal tubule blood flow and/or permeability, glomerular damage, etc.), anti-vascular endothelial growth factor (anti-VEGF) toxicities, anti-angiogenesis toxicities, cardiovascular complications, arterial thromboembolic events (e.g., myocardial infarction, angina, cardiac ischemia, cerebrovascular event, transient ischemic event, stroke, cerebral ischemia, etc.), cerebrovascular complications and the like, including any combination thereof, as would be known in the art), by administering an effective amount of a phosphodiesterase inhibitor to a subject in need thereof, as described herein.

Application to other diseases associated with abnormal vascular function are also possible, including conditions of abnormal wound healing, such as decubitus and other pressure and stasis ulcers, and conditions with compromised or abnormal wound healing related to diabetes and peripheral vascular disease. Related applications would include embedding the phosphodiester inhibitor into other topically applied clinical materials, such as bandage and suture materials. It is possible that topical or embedded phosphodiester inhibitor may also improve the speed, strength, or cosmesis of wound healing.

As used herein, the term "condition" or "condition of interest" refers to those conditions involving inflammatory and/or vascular pathologies. In some embodiments, the condition comprises inflammatory and/or vascular disorders associated with drugs such as chemotherapy drugs, anti-angiogenesis drugs and/or other drugs that have anti-vascular side effects. Such disorders include, but are not limited to, PPE and/or drug toxicity associated reactions, disorders and/or symptoms.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle administration). In the methods of this invention, the phosphodiesterase inhibitor of this invention may be administered alone and/or simultaneously with one or more other compounds. In some embodiments, the compounds may be administered sequentially, in any order. It will be appreciated that the actual method and order of administration will vary according to, inter alia, the particular preparation of compound(s) being utilized, the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramascular, intravenous, intraventricular, intrathecal, and subcutaneous routes. In particular embodiments, the term "administering" refers to topical (i.e., application of the compound to the skin/dermal surface of a patient). The use of topical administration would allow a potentially higher local concentration, thereby improving activity and/or reducing the risk of systemic toxicity. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition such as PPE and/or other drug toxicity associated reactions, disorders and/or symptoms. The term "prevent" refers to the ability to keep a condition such as PPE and/or other drug toxicity associated reactions, disorders and/or symptoms from happening or existing, as well as to delay or diminish onset.

The compounds of the present invention, and pharmaceutical compositions thereof, can be administered to subjects as described herein for prophylactic and/or therapeutic purposes.

In therapeutic applications, the phosphodiesterase inhibitor is administered to a subject that already has PPE and/or other drug toxicity associated reactions, disorders and/or symptoms. Those subjects in the incubation phase or the acute phase of the reaction or disorder may be treated with one or more phosphodiesterase inhibitors separately or in conjunction with other treatments, as appropriate and as would be known to one of skill in the art.

Furthermore, in therapeutic applications, a phosphodiesterase inhibitor is administered to a subject in an amount sufficient to effectively treat, or at least partially arrest, diminish and/or reduce, symptoms and/or complications of PPE and/or of other drug toxicity associated reactions, disorders and/or symptoms. An amount adequate to accomplish this is defined as an "effective dose" or "therapeutically effective dose." Amounts effective for this use will depend in part on the compound used, the manner of administration, the stage and severity of the disease being treated, the weight and general state of health of the subject, and the judgment of the prescribing physician.

Further, the compositions and methods of this invention can be used prophylactically to prevent, treat, reduce, and/or ameliorate conditions associated with drug-induced toxicities such as PPE and/or of other drug toxicity associated reactions, disorders and/or symptoms. Effective amounts are as described herein. Additionally, one of ordinary skill in the art would also know how to adjust or modify prophylactic treatments, as appropriate.

Therapeutic administration may begin at the first sign of disease or detection of symptoms of PPE (e.g., redness, swelling, pain, etc. of the hand(s) and/or foot/feet) and/or of other drug toxicity associated reactions, disorders and/or symptoms as described herein. Prophylactic administration may begin prior to any signs or symptoms of PPE and/or other drug toxicity associated reactions, disorders and/r symptoms. Such prophylactic administration would be for a subject in need thereof, e.g., a subject to whom one or more drugs associated with PPE and/or of other drug toxicity associated reactions, disorders and/or symptoms is to be administered. Thus, the phosphodiesterase inhibitor can be administered prior to and/or concurrently with the administration of a drug associated with PPE and/or of other drug toxicity associated reactions, disorders and/or symptoms, but prior to the onset of symptoms of PPE and/or of other drug toxicity associated reactions, disorders and/or symptoms.

The pharmaceutical compositions for therapeutic and/or prophylactic treatment are intended for mucosal (oral, nasal, rectal, urethral, vaginal, tracheal, etc.), parenteral, topical, or local administration (Note that mucosal administration is different from topical administration, as mucosal administration refers to application of the compound to a mucosal surface such as a surface of the respiratory tract, gastrointestinal tract, reproductive tract, etc.).

In particular embodiments, the pharmaceutical compositions are administered topically, e.g., applied to the affected area on the skin (e.g., palms of hands and/or soles of feet). Other topical administrations may be to an airway surface, such as by droplet administration to a nasal surface or by inhalation administration of aerosolized particles to a nasal surface or the surfaces of other airway passages; or to skin such as for the treatment of wounds or scarring as described herein. Thus, the invention provides compositions for topical (mucosal or non-mucosal) or parenteral administration which can comprise a compound of the present invention (e.g., a phosphodiesterase inhibitor) dissolved or suspended in a pharmaceutically acceptable carrier, such as an aqueous carrier as a pharmaceutical composition. In some embodiments, a pharmaceutical composition can comprise albumin, liposomes, nanoparticles, etc., as are known in the art.

In some embodiments, the pharmaceutical composition can be administered topically. A variety of aqueous carriers may be used, e.g., water, buffered water, 0.9% saline, 0.3% glycine, hyaluronic acid and the like. These compositions may-be sterilized by conventional, well known sterilization techniques, or may be sterile filtered. The resulting compositions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc. Alternatively, the pharmaceutical compositions according the present disclosure may also be in dry powder formulations.

Further embodiments of the present invention include a kit for the treatment and/or prevention of PPE and/or of other drug toxicity associated reactions, disorders and/or symptoms, comprising a pharmaceutical composition comprising a phosphodiesterase inhibitor, and instructions for use to treat and/or prevent PPE and/or of other drug toxicity associated reactions, disorders and/or symptoms. In some embodiments of the kit of this invention, the phosphodiesterase inhibitor can be formulated for topical administration.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

EXAMPLES

Four patients were treated with topical sildenafil for PPE, two with PPE related to capecitabine and two with PPE related to sunitinib. In all three patients, their PPE-related symptoms significantly improved as a result of topical sildenafil treatment. This initial clinical experience was outside the context of formal clinical trials, since no such trials were available. This treatment was also initiated because these patients had no therapeutic alternatives for their cancer and were deriving robust clinical benefit that would have likely been jeopardized by stopping or further reducing their anti-cancer treatment.

The first patient had both metastatic pancreatic cancer and a history of mild Raynaud's syndrome. Treatment with capecitabine resulted in a minor response but was complicated by grade 2-3 PPE and a flare of her Raynaud's syndrome, leading to painful ulcers in several finger tips. After failure of calcium channel blockers, topical 2% sildenafil was applied to the ulcers and within a week there was marked improvement in the patient's pain and in the size and depth of the digital ulcers. Importantly, the PPE adjacent to the ulcers also improved. Topical sildenafil was then applied to the full palm of one hand with significant improvement in PPE. Similar improvements were then seen when the other palm and the soles were treated.

The second patient was a woman with metastatic colon cancer, who had a dramatic anti-tumor response with capecitabine, oxaliplatin and bevacizuamb. However, her treatment was complicated by grade 2-3 PPE that persisted despite dose holdings and reductions. The patient was switched to a regimen of infusional 5FU plus irniotecan and bevacizumab, which also was associated with grade 2-3 PPE in this patient. Administration of 5FU was held due to the severity and persistence of the hand-foot syndrome. Topical sildenafil was applied to only the left hand. The patient noted improvement in the pain and redness of the left hand as noted by day 8. By day 72, the hand-foot syndrome had resolved in both hands.

The third patient was a man with a gastro-intestinal stromal tumor (GIST) refractory to imatinib, who was being treated with sunitinib. Despite a gratifying response to sunitinib, he experienced grade 3 sunitinib-related PPE that required frequent dose holding and reduction. He was treated with topical 2% sildenafil three times daily. To ensure activity in the setting of potentially significant costs for custom formulation, this patient applied topical sildenafil to only his left hand. He experienced no side effects, such as headache, chest pain, lightheadedness, and no spontaneous erections during this month of treatment. After only 3 doses (1 day) he noticed an improvement on the tenderness and redness of his hands. By one week, pain, redness and blisters were markedly improved. After 4 weeks, redness was markedly better; pain had resolved; multiple blisters, cracks, and callousness had all resolved essentially completely. The improvement was "like day and night." The right hand had all of these complications. These were severe enough that the patient had difficulty physically closing his hand more than halfway due to skin thickening as well as pain. His left hand was completely flexible. After administration to both hands, he was able for the first time in many months to shake hands and make a fist without difficulty or pain and he restarted playing his guitar in his church choir. This patient later was dosed with 1% topical sildenafil once per week. In addition, this patient experienced sunitinib-induced gastrointestinal toxicities (enteritis, diarrhea), which were treated with oral sildenafil to allow systemic absorption. The initial dose was 50 mg oral sildenafil daily. This rapidly improved his gastrointestinal toxicities and his hand-foot syndrome, within 1 day. Thereafter lower doses were used on an as needed basis, including a quarter tablet (50 mg size) given once or twice per week.

A fourth patient was a woman with metastatic angiosarcoma, who was treated with sunitinib for over four years. Her treatment was complicated by grade 3 PPE that required reduction of her sunitinib from 50 mg given daily to 12.5 mg given every other day (i.e., three times per week; e.g., Monday-Wednesday-Friday). Due to tumor progression on low does sunitinib, her dose of sunitinib was increased to 37.5 mg per day (7 days per week), which caused her PPE to return. Her hand-foot syndrome was grade 1 when she started treatment with topical sildenafil 2% (with a cold cream base) to only her right hand and right foot. The right hand and foot improved markedly within 1-2 weeks. The untreated hand and foot continued to worsen. Of note, the patient's tumor showed signs of response to the higher dose of sunitinib after only 1 month at the higher dose.

Since each of these patients initially had only one affected skin region treated, followed by treatment of the other similarly affected regions, each patient was able to serve as her/his own control. No local or systemic side effects were experienced in any of these patients. Furthermore, no patient had any suggestion of an adverse impact on their cancer's response to treatment.

Taken together, the known pathophysiology of PPE and these four cases indicate that topical sildenafil may ameliorate the severity of PPE. Oral administration also resulted in improvement of systemic toxicities.

Variations and modifications of the herein described methods and compositions will undoubtedly suggest themselves to those skilled in the art. Accordingly, the foregoing description should be taken as illustrative and not in a limiting sense.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of exemplary embodiments and are not intended as limitations on the scope of the invention. Changes therein and other uses will occur to those skilled in the art which are encompassed within the spirit of the invention as defined by the scope of the claims provided herein below.

REFERENCES

1. Bayer HealthCare Pharmaceuticals. Sorafenib Prescribing Information. 2009.
2. Hoffman La Roche Laboratories Inc. Capecitabine Prescribing Information. 2006.
3. Ortho Biotech. Doxil Prescribing Information. 2007.
4. Pfizer Labs. Sunitinib malate Prescribing Information. 2009.
5. Lorusso D, Di Stefano A, Carone V, Fagotti A, Pisconti S, Scambia G. "Pegylated liposomal doxorubicin-related palmar-plantar erythrodysesthesia ('hand-foot' syndrome)" *Ann Oncol.* 2007; 18(7):1159-64.
6. Walko C M, Lindley C. "Capecitabine: a review" *Clin Ther.* 2005; 27(1):23-44.
7. Lacouture M E, Wu S, Robert C, Atkins M B, Kong H H, Guitart J, et al. "Evolving strategies for the management of hand-foot skin reaction associated with the multitargeted kinase inhibitors sorafenib and sunitinib" *Oncologist* 2008;13(9):1001-11.

What is claimed is:

1. A method of treating, ameliorating palmar-plantar erythrodysesthesia (PPE) in a subject that has PPE associated with treatment of capecitabine or sutinib comprising topically administering to the subject an effective amount of a phosphodiesterase type 5 inhibitor selected from the group consisting of sildenfil, tadalafil and vardenafil, thereby treating or ameliorating PPE in the subject that has PPE associated with treatment of capecitabine or sutinib.

* * * * *

UNITED STATES PATENT AND TRADEMARK OFFICE
CERTIFICATE OF CORRECTION

PATENT NO. : 9,220,713 B2
APPLICATION NO. : 13/502209
DATED : December 29, 2015
INVENTOR(S) : Hurwitz Page 1 of 1

It is certified that error appears in the above-identified patent and that said Letters Patent is hereby corrected as shown below:

In the Specification:
Column 3, Line 24: Please correct "thereof A drug" to read -- thereof. A drug --

In the Claims:
Column 12, Claim 1, Line 15: Please correct "treating, ameliorating"
to read -- treating or ameliorating --

Column 12, Claim 1, Line 20: Please correct "sildenfil," to read -- sildenafil, --

Signed and Sealed this
Twenty-eighth Day of June, 2016

Michelle K. Lee
*Director of the United States Patent and Trademark Office*